US012673177B2

(12) United States Patent
Tyke et al.

(10) Patent No.: US 12,673,177 B2
(45) Date of Patent: Jul. 7, 2026

(54) INTEGRATED HUMIDIFIER WATER INGRESS PROTECTION

(71) Applicant: KONINKLIJKE PHILIPS N.V., Eindhoven (NL)

(72) Inventors: Anthony John Tyke, Monroeville, PA (US); Mark Barclay, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1033 days.

(21) Appl. No.: 17/676,325

(22) Filed: Feb. 21, 2022

(65) Prior Publication Data

US 2022/0265954 A1 Aug. 25, 2022

Related U.S. Application Data

(60) Provisional application No. 63/151,956, filed on Feb. 22, 2021.

(51) Int. Cl.
*A61M 16/16* (2006.01)

(52) U.S. Cl.
CPC ................................... *A61M 16/16* (2013.01)

(58) Field of Classification Search
CPC ............... A61M 16/16; A61M 16/109; A61M 2205/21; A61M 16/14; A61M 16/142
USPC ............ 128/203.16, 203.17, 203.25, 203.26, 128/203.27, 204.14
See application file for complete search history.

(56) References Cited

U.S. PATENT DOCUMENTS

| | | | |
|---|---|---|---|
| 3,806,102 A | * | 4/1974 | Valenta ................. A61M 16/16 261/DIG. 65 |
| 6,398,197 B1 | | 6/2002 | Dickinson |
| 7,614,398 B2 | | 11/2009 | Virr |
| 9,174,016 B2 | | 11/2015 | Barclay |
| 9,707,370 B2 | | 7/2017 | Smith |
| 2017/0361053 A1 | | 12/2017 | Dimatteo |

(Continued)

FOREIGN PATENT DOCUMENTS

CN 105963842 A * 9/2016 ........ A61M 16/0057

OTHER PUBLICATIONS

CN-105963842-A Translation (Year: 2025).*

(Continued)

*Primary Examiner* — Kendra D Carter
*Assistant Examiner* — Keira Eileen Callison
(74) *Attorney, Agent, or Firm* — Brynne J. Corcoran

(57) ABSTRACT

A humidifier for a CPAP pressurized air generator includes a water tank with a port arrangement protruding into the interior of the tank. The port arrangement includes an inlet, a chimney surrounding the inlet, an outlet, and drain channels. The inlet receives pressurized air output by the CPAP generator and outputs the pressurized air at an opening disposed higher than a maximum fill height of the water tank. The chimney directs the pressurized air output by the inlet to flow out of a number of egress slots and into the tank, the egress slots being disposed lower than the output height of the inlet. The pressurized air gets humidified in the tank and subsequently flows out of the outlet into a conduit for delivery to the airway of a patient. The drain channels divert water out of the water tank once the maximum fill height is reached.

16 Claims, 9 Drawing Sheets

(56)          References Cited

U.S. PATENT DOCUMENTS

2018/0333556 A1* 11/2018 Ormrod ........... A61M 16/0051

OTHER PUBLICATIONS

Labeled Paragraph Numbers for CN 105963842 A (Year: 2025).*
DS2_Advanced_User_Draft.pdf.—p. 4: refers to "integrated humidi-
fier"—p. 7: very bottom has warning "do not attempt to fill tank
while connected to device".
DS2_Base_User_Draft (002).pdf—p. 4: refers to "integrated humidi-
fier"—p. 7: very bottom has warning "do not attempt to fill tank
while connected to device".
https://fccid.io/THO1141623/External-Photos/DSX520-models-
4687713.

* cited by examiner

1

P

6

4

2

4

10

100

6

106

INTEGRATED HUMIDIFIER WATER INGRESS PROTECTION

CROSS REFERENCE TO RELATED APPLICATION

This patent application claims the priority benefit under 35 U.S.C. § 119(e) of U.S. Provisional Application No. 63/151,956 filed Feb. 22, 2021, the contents of which are herein incorporated by reference.

BACKGROUND OF THE INVENTION

1. Field of the Invention

The present invention pertains to humidifiers for use in airway pressure support systems for delivering a flow of a humidified gas to the airway of a patient, and in particular, to water tanks of such humidifiers and arrangements for preventing the backflow of water from a water tank into the pressure generating unit of an airway pressure support system.

2. Description of the Related Art

Patient interfaces are used to deliver a flow of breathing gas to a user in a variety of contexts. Pressurized breathing gas in particular is often used to treat medical disorders. For example, it is known to use positive airway pressure (PAP) therapy to treat conditions such as chronic obstructive pulmonary disease (COPD) or sleep apnea syndrome, in particular, obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle.

Humidifiers are often included with CPAP devices, as delivering humidified air to the airway of a patient increases comfort and increases compliance with CPAP therapy. In CPAP devices that include humidifiers, the humidifier includes a tank of water and means for heating the water. The pressurized air generated by the CPAP generator is blown over the heated water's surface in order to capture and deliver humidified air to the patient's airway. On these devices, the water chamber itself is generally much larger than the volume of water they are intended to contain. This is to allow for operation of the humidifier under abnormal conditions. Abnormal conditions include being tilted up to 20° in all directions as well as rotated 360° in all directions (including upside down) in order to conform to certain applicable ISO standards and to ensure that foreseen misuse cases are accounted for. Under these test conditions, no water is to egress from the water chamber and ingress into the CPAP generator to which the humidifier is attached, as the CPAP generator houses electrical and mechanical components (referred to hereinafter as "electromechanical components"). In order to avoid such ingress, some CPAP devices include a "dry box" (a compartment between the water chamber and the electromechanical CPAP device components to capture any water that may egress from the water chamber) and/or a valve system that can prevent water from leaving the water chamber. Both of these standard solutions are meant to protect the CPAP generator electromechanical components from water.

Water ingress to a CPAP generator when used in conjunction with a humidifier can cause catastrophic damage to the electronics and blower of the device. More importantly, water inside the CPAP generator where electricity is present creates a potential safety issue. When the CPAP generator and humidifier are operated in the normal recommended orientation (i.e., sitting flat on a surface such as a nightstand), water contained in the humidifier will not present any operating or safety issues, provided that the user abides by the fill volume specified by the manufacturer when filling the humidifier with water. The issue of water ingress to the CPAP generator mainly occurs during normal misuse case scenarios such as overfilling the humidifier past the maximum fill volume as well as when the user does not empty the water out of the humidifier before moving or traveling with the device.

Currently, the most common method used for water ingress protection in a CPAP humidifier system is volumetric water ingress protection. This method requires that the tank volume far exceed the volume required for the water in order to have a location for the water to displace under conditions such as tilting or rotation of the device in order to prevent water from the humidifying chamber flowing back into the CPAP pressure generating device. This method is extremely effective in providing water ingress protection for the pressure generating device, but the large tank volume required for this method is a disadvantage, as the large tank volume drives a larger overall device footprint and generally requires supplemental protection such as a dry box or valve.

There is thus room for improvement in the design of water ingress protection arrangements of humidifiers for CPAP devices.

SUMMARY OF THE INVENTION

Accordingly, it is an object of the present invention to provide, in one embodiment, a water tank structured to hold a volume of water and humidify air output by a pressurized air generator. The water tank includes a port arrangement extending inward from a wall of the water tank to an interior of the water tank, and the port arrangement comprises an inlet comprising a passage having a first end structured to receive the pressurized air output by the pressurized air generator and a second end disposed opposite the first end, the second end being disposed at a height above a maximum fill height of the water tank, a chimney surrounding the second end of the inlet and comprising a number of egress slots disposed at a height lower than the second end of the inlet and in fluid communication with the interior of the water tank, and an outlet comprising a passage having a first end in fluid communication with the interior of the water tank and a second end disposed opposite the first end and in fluid communication with an exterior of the water tank. The lowest edge of the number of egress slots is disposed at a height above the maximum fill height of the water tank, and the portion of the water tank exclusive of the port arrangement and exclusive of the volume of water comprises the vapor region of the water tank.

In another embodiment, a humidifier structured to humidify air output by a pressurized air generator comprises a water tank structured to hold a volume of water and a lid selectively coupled to the water tank in order to enclose the interior of the water tank. The water tank includes a port arrangement extending inward from a wall of the water tank to an interior of the water tank, and the port arrangement comprises an inlet comprising a passage having a first end structured to receive the pressurized air output by the pressurized air generator and a second end disposed opposite the first end, the second end being disposed at a height above a maximum fill height of the water tank, a chimney surrounding the second end of the inlet and comprising a number of egress slots disposed at a height lower than the second end of the inlet and in fluid communication with the interior of the water tank, and an outlet comprising a passage having a first end in fluid communication with the interior of the water tank and a second end disposed opposite the first end and in fluid communication with an exterior of the water tank. The lowest edge of the number of egress slots is disposed at a height above the maximum fill height of the water tank, and the portion of the water tank exclusive of the port arrangement and exclusive of the volume of water comprises the vapor region of the water tank.

In another embodiment, a respiratory therapy device for providing humidified pressurized air to an airway of a patient includes a pressurized air generator structured to output pressurized air, a humidifier structured to humidify the pressurized air, and a heat source. The humidifier comprises a water tank structured to hold a volume of water and a lid selectively coupled to the water tank in order to enclose the interior of the water tank. The heat source is structured to heat the volume of water and to be selectively powered on. The water tank includes a port arrangement extending inward from a wall of the water tank to an interior of the water tank, and the port arrangement comprises an inlet comprising a passage having a first end structured to receive the pressurized air output by the pressurized air generator and a second end disposed opposite the first end, the second end being disposed at a height above a maximum fill height of the water tank, a chimney surrounding the second end of the inlet and comprising a number of egress slots disposed at a height lower than the second end of the inlet and in fluid communication with the interior of the water tank, and an outlet comprising a passage having a first end in fluid communication with the interior of the water tank and a second end disposed opposite the first end and in fluid communication with an exterior of the water tank. The lowest edge of the number of egress slots is disposed at a height above the maximum fill height of the water tank, and the portion of the water tank exclusive of the port arrangement and exclusive of the volume of water comprises the vapor region of the water tank.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 2A:
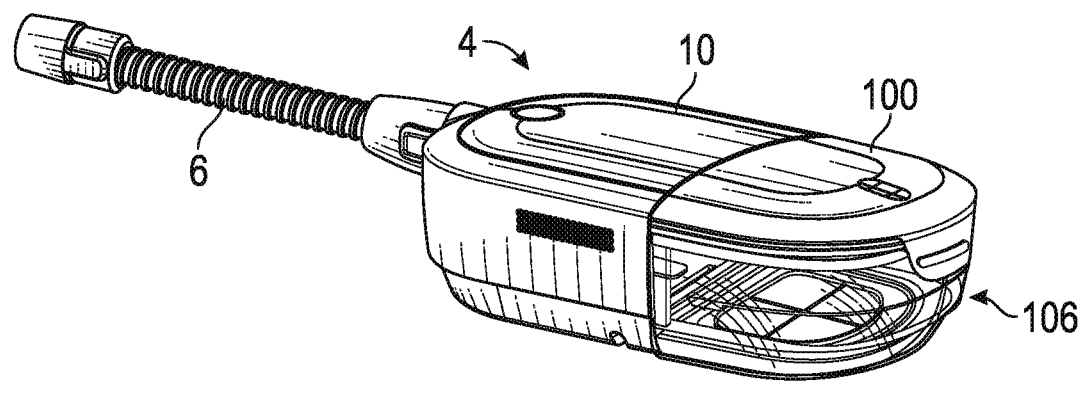
FIG. 2A is an isometric view of a respiratory therapy machine for the respiratory therapy system shown in FIG. 1
Figure 2B:
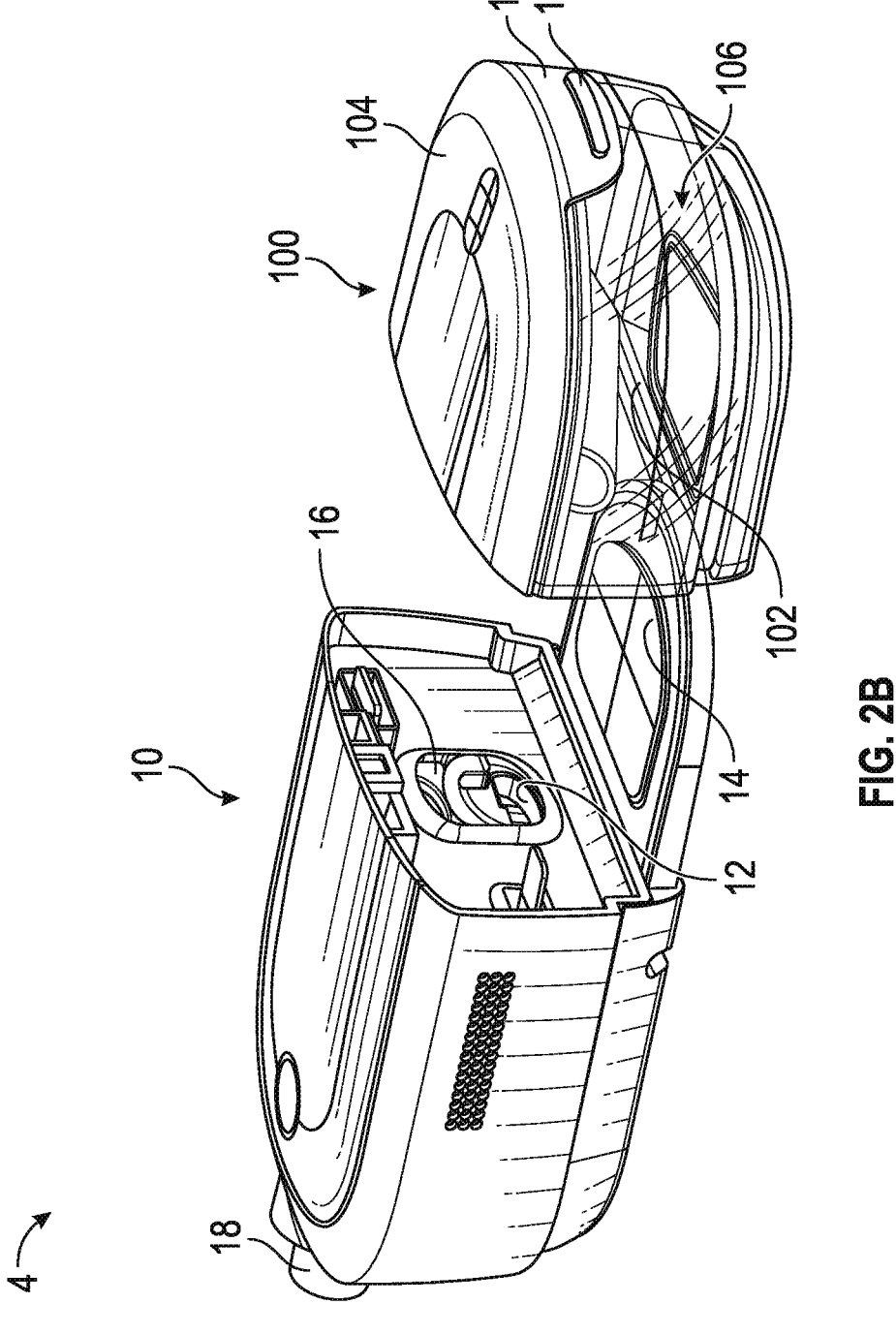
Figure 2C:
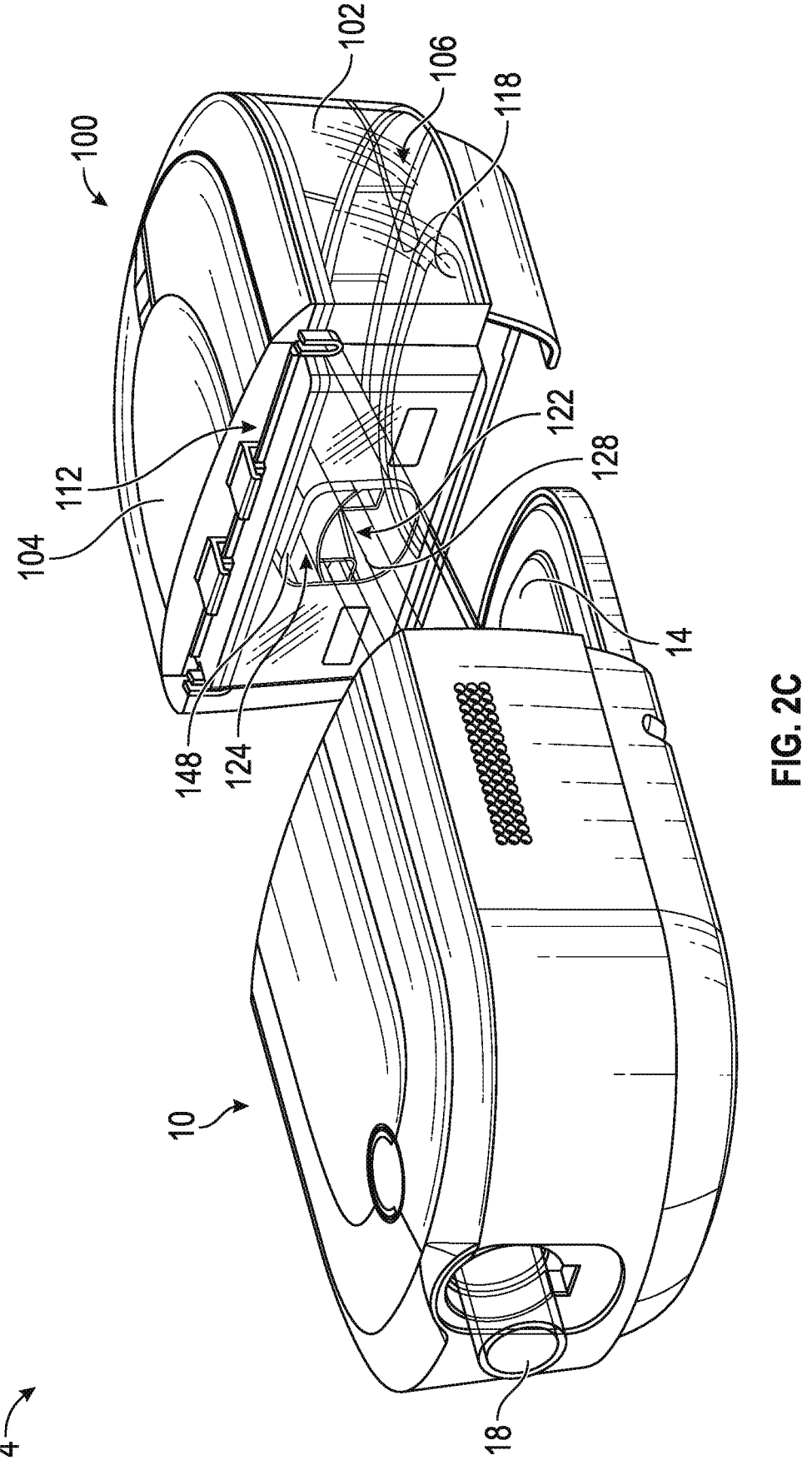
Figure 3A:
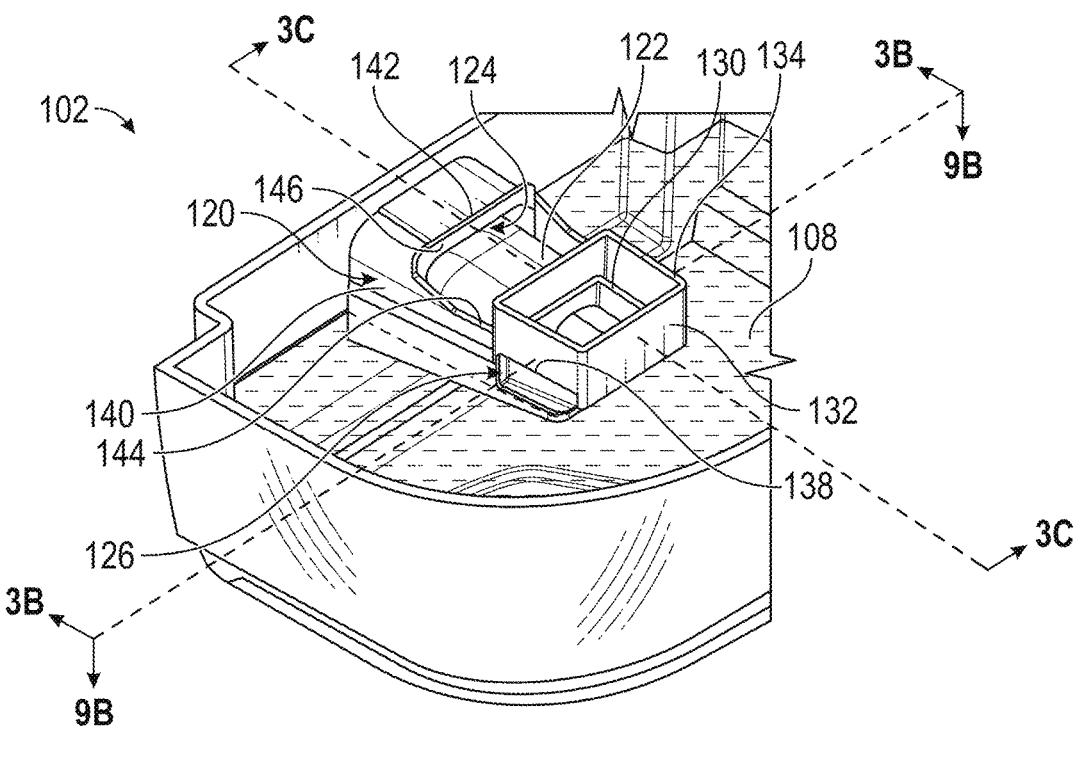
Figure 3B:
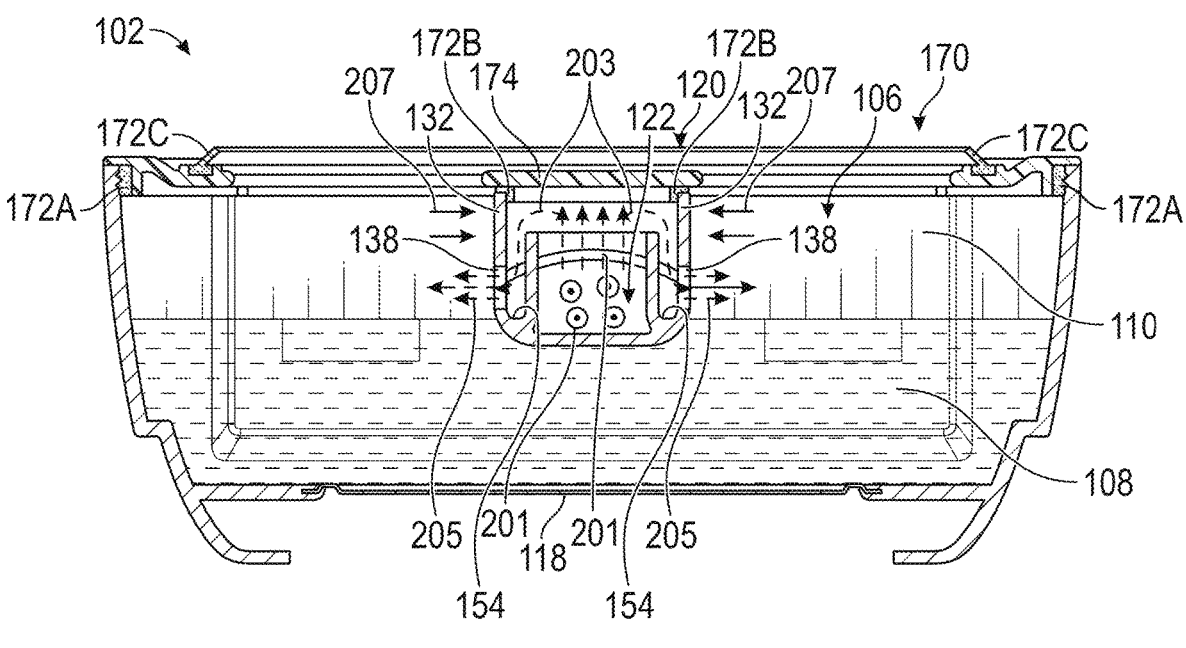
Figure 3C:
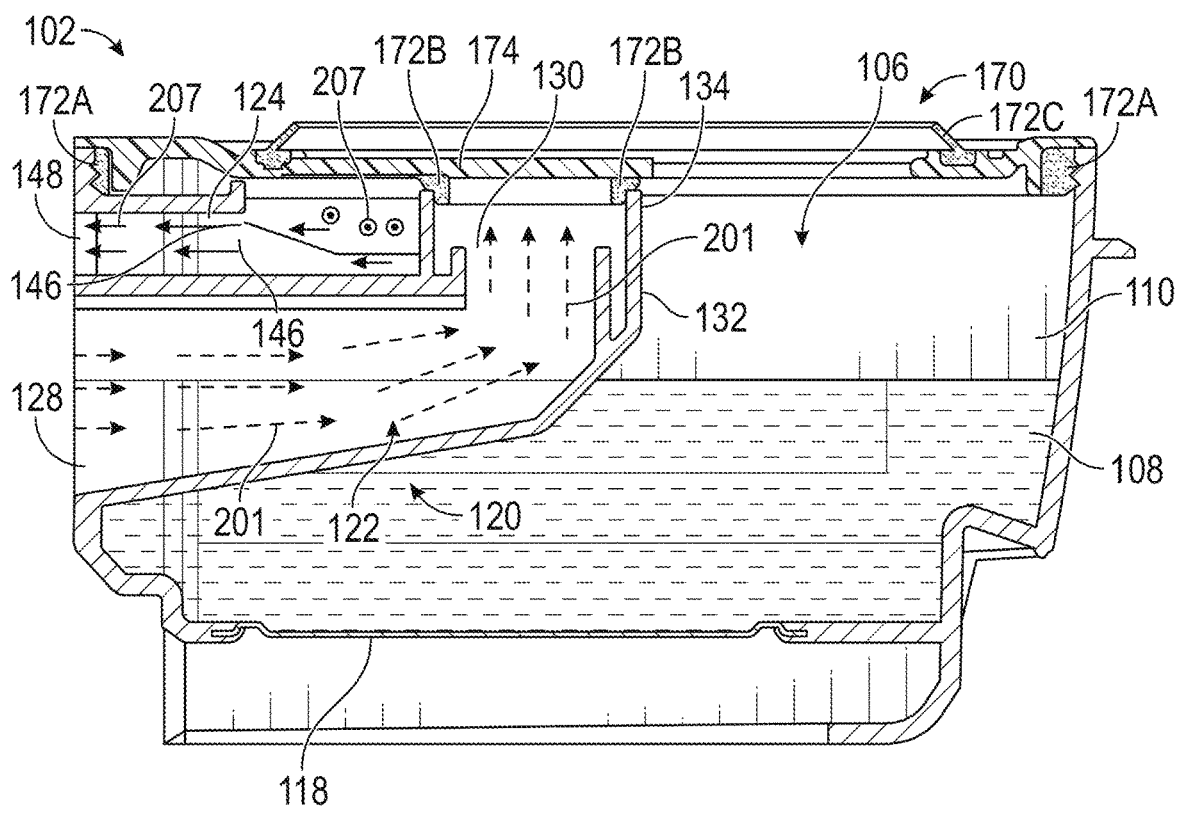
Figure 4A:
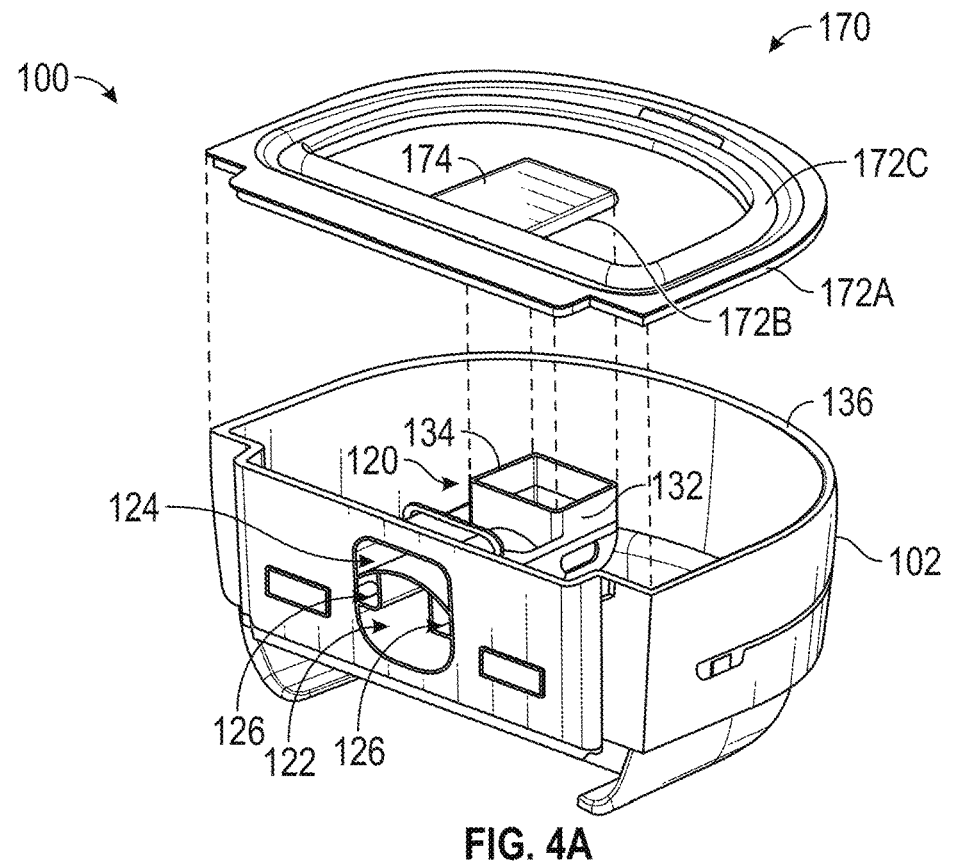
Figure 4B:
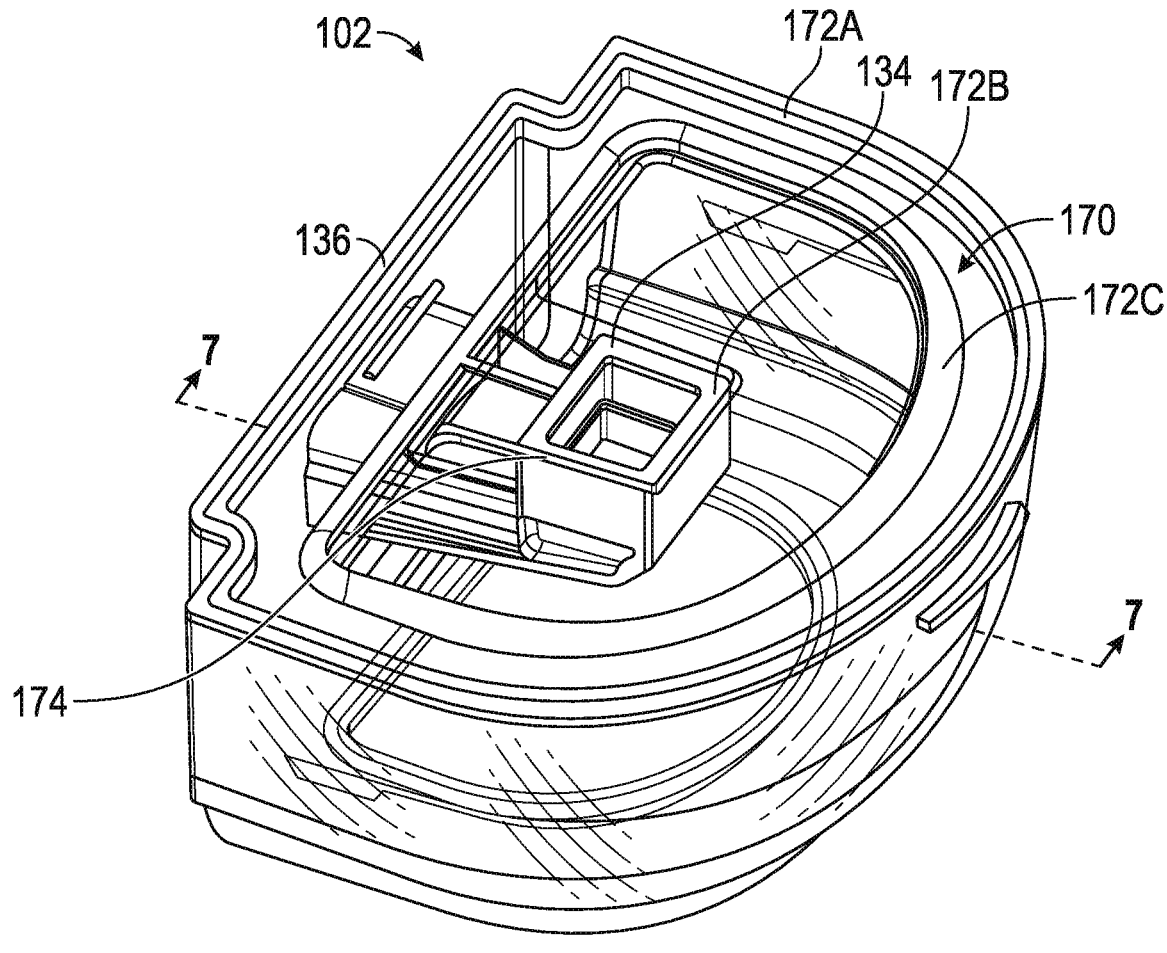
Figure 5:
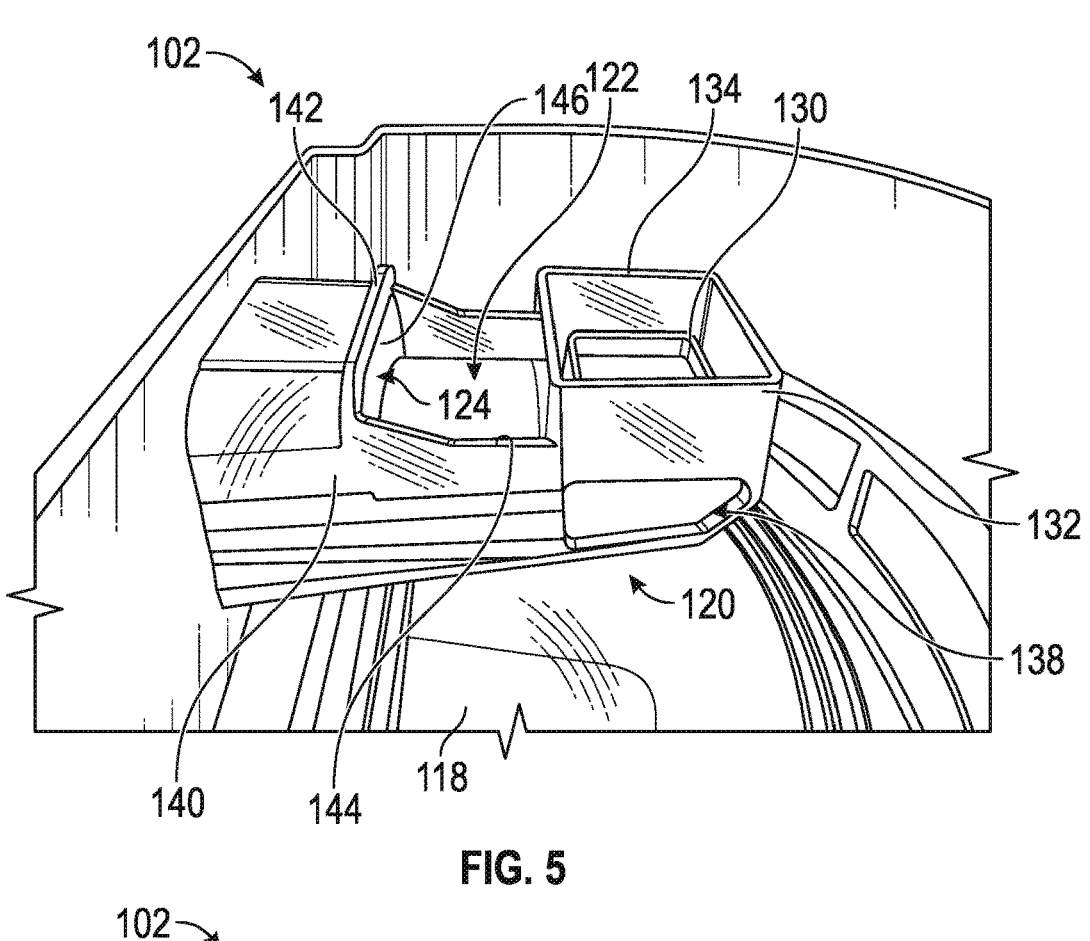
Figure 6:
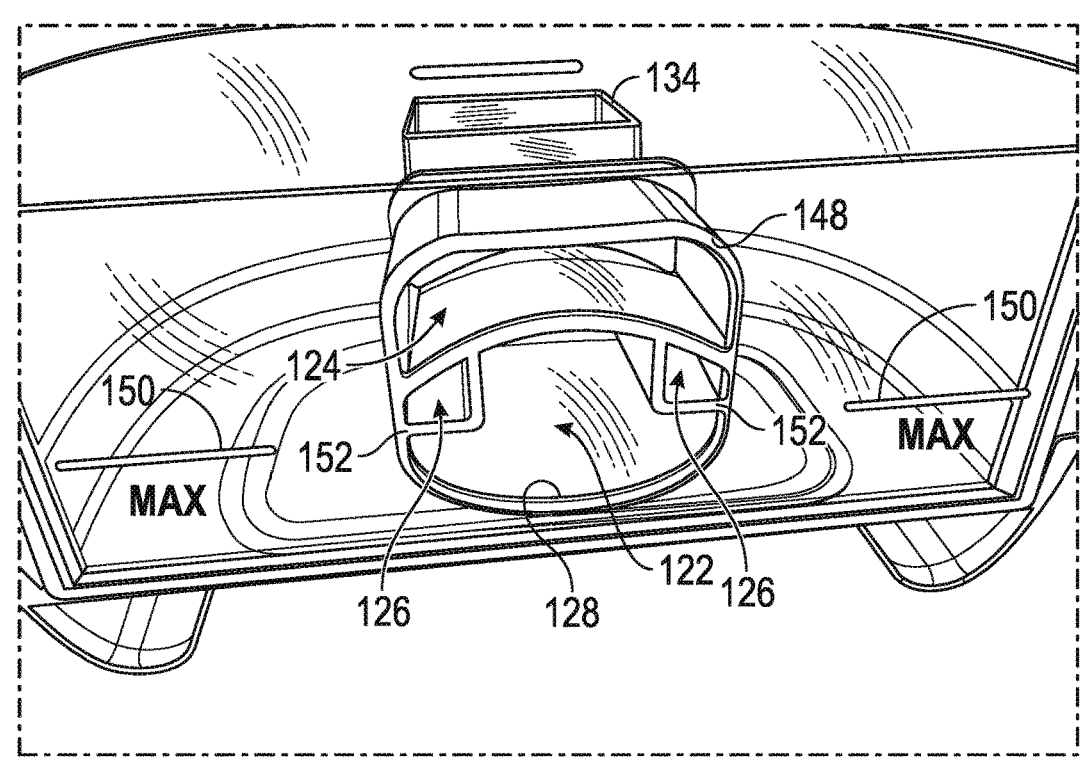
Figures 7, 8:
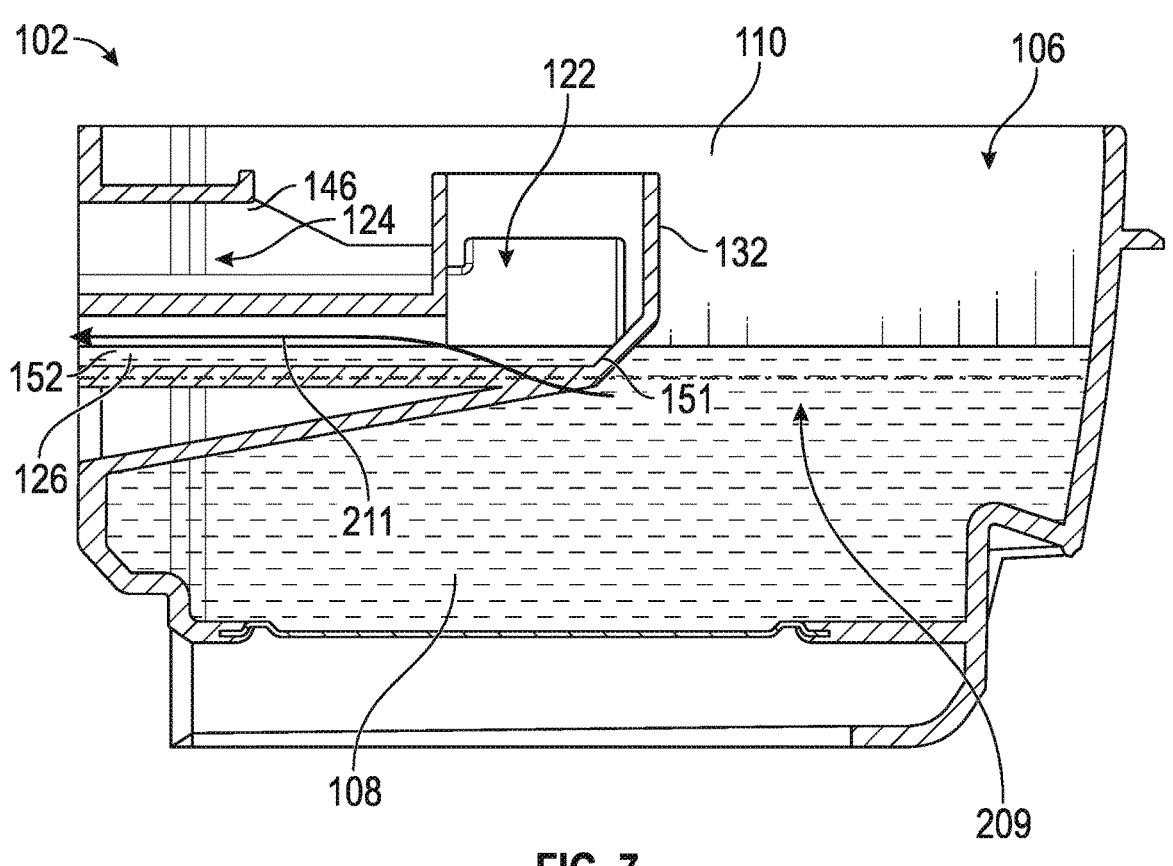
Figure 9A:
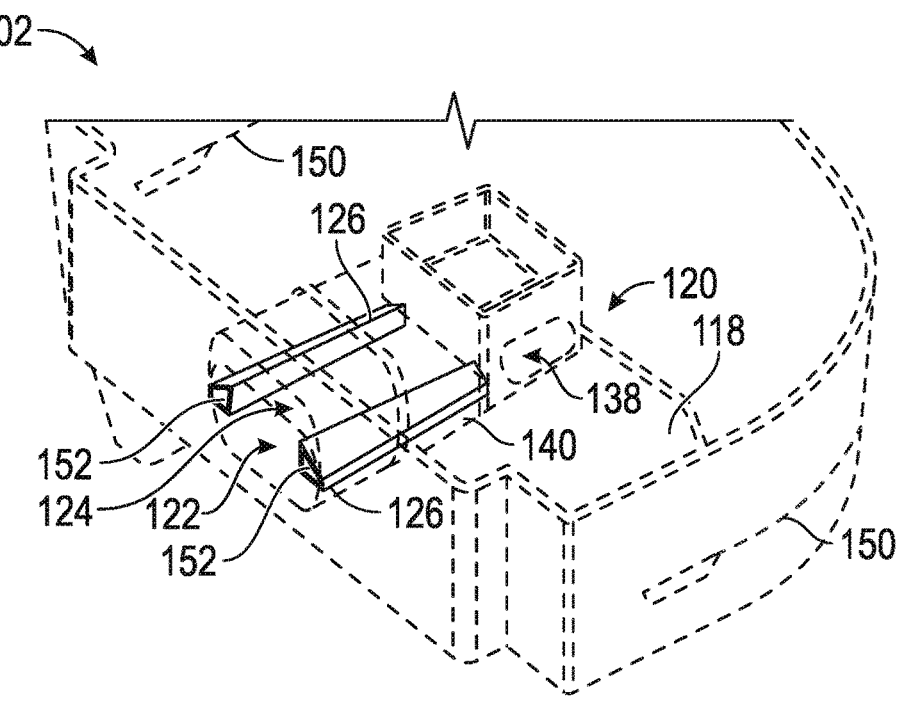
Figure 9B:
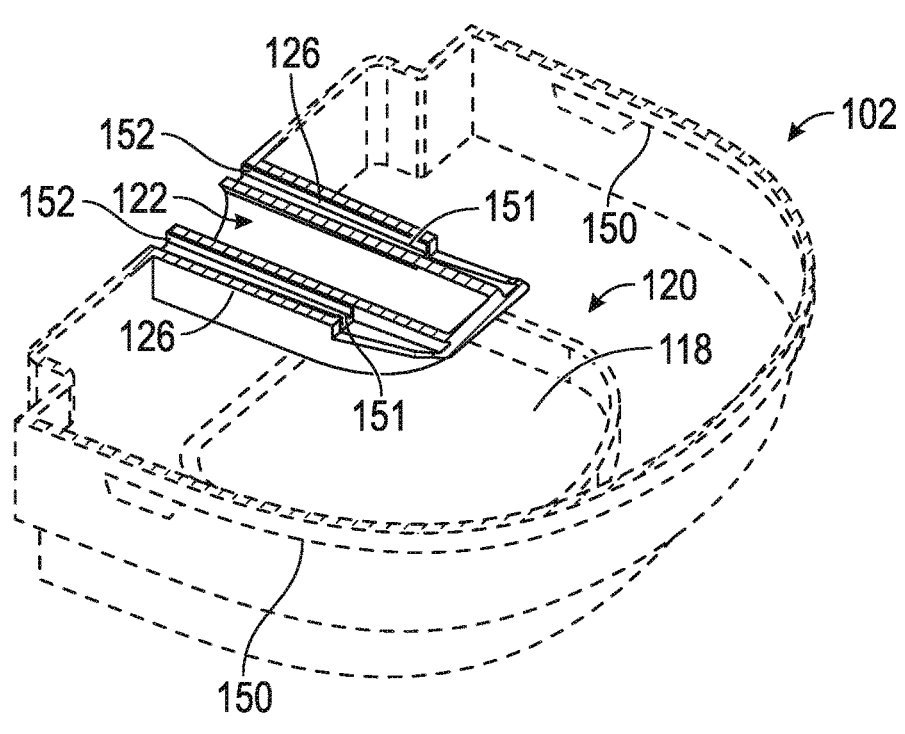

4 comprising a pressurized air generator and a humidifier in accordance with an exemplary embodiment of the present invention;

FIG. 2B is an isometric view of the respiratory therapy machine of FIG. 2A shown with the humidifier separated from the rest of the respiratory therapy machine;

FIG. 2C is an alternative isometric view of the respiratory therapy machine of FIG. 2A shown with the humidifier separated from the rest of the respiratory therapy machine;

FIG. 3A is a partial overhead isometric view of the humidifier shown in FIGS. 2A-2C with the lid removed showing the inlet, the outlet, and the overfill channels of the humidifier in accordance with an exemplary embodiment of the present invention;

FIG. 3B is a sectional view of the humidifier of FIG. 3A as indicated by line 3B-3B in FIG. 3A, with arrows representing the path of pressurized air flow through the humidifier in accordance with an exemplary embodiment of the present invention;

FIG. 3C is a sectional view of the humidifier of FIG. 3A as indicated by line 3C-3C in FIG. 3A with arrows representing the path of pressurized air flow through the humidifier in accordance with an exemplary embodiment of the present invention;

FIG. 4A is an isometric view of an inner seal designed to provide an airtight seal between the lid and the water tank of the humidifier of FIGS. 2A-2C in accordance with an exemplary embodiment of the present invention;

FIG. 4B is an isometric view of the humidifier of FIGS. 2A-2C shown with the lid removed depicting surfaces of the water tank and the port arrangement of the humidifier that are engaged by the inner seal shown in FIG. 4A when the lid of the humidifier is closed, in accordance with an exemplary embodiment of the present invention;

FIG. 5 is a detail isometric view of a portion of the humidifier of FIGS. 2A-2C shown with the lid removed;

FIG. 6 is a detail isometric view of another portion of the humidifier of FIGS. 2A-2C shown with the lid removed;

FIG. 7 is a sectional view of the humidifier of FIG. 4B along a non-central plane as indicated by line 7-7 in FIG. 4B, showing how a drain passage system of the humidifier directs excess water out of the water tank when the water tank is overfilled, in accordance with an exemplary embodiment of the present invention;

FIG. 8 is a detail isometric view of the port arrangement of the humidifier of FIGS. 2A-2C showing how water that flows into the port arrangement from the water tank during physical disturbance of the humidifier is channeled by a gutter out of the port arrangement and back into the water tank, in accordance with an exemplary embodiment of the present invention;

FIG. 9A shows a partial overhead isometric view of the humidifier shown in FIGS. 2A-2C with the lid removed showing the drain passages of the humidifier in solid line and other features of the humidifier in phantom line in order to show the entire length of the drain passages; and FIG. 9B is a sectional view of the humidifier of FIG. 3A as indicated by line 9B-9B in FIG. 3A, showing the drain passages and port arrangement in solid line and other features of the humidifier in phantom line in order to show how the drain passages extend from entry ports located in the interior of the water tank to exit ports located on the front side of the humidifier, in accordance with an exemplary embodiment of the present invention.

DETAILED DESCRIPTION OF EXEMPLARY
EMBODIMENTS

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled in direct contact with each other. As used herein, "fixedly coupled" or "fixed" means that two components are coupled so as to move as one while maintaining a constant orientation relative to each other. As used herein, "movably coupled" means that two components are coupled so as to allow at least one of the components to move in a manner such that the orientation of the at least one component relative to the other component may change without the components being uncoupled.

As used herein, the statement that two or more parts or components are "integrated" shall mean that the parts or components are produced separately and subsequently joined together to produce a larger body.

As used herein, the term "number" shall mean one or an integer greater than one (i.e., a plurality).

As used herein, the word "unitary" means a component is created as a single piece or unit. That is, a component that includes pieces that are created separately and then coupled together as a unit is not a "unitary" component or body.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
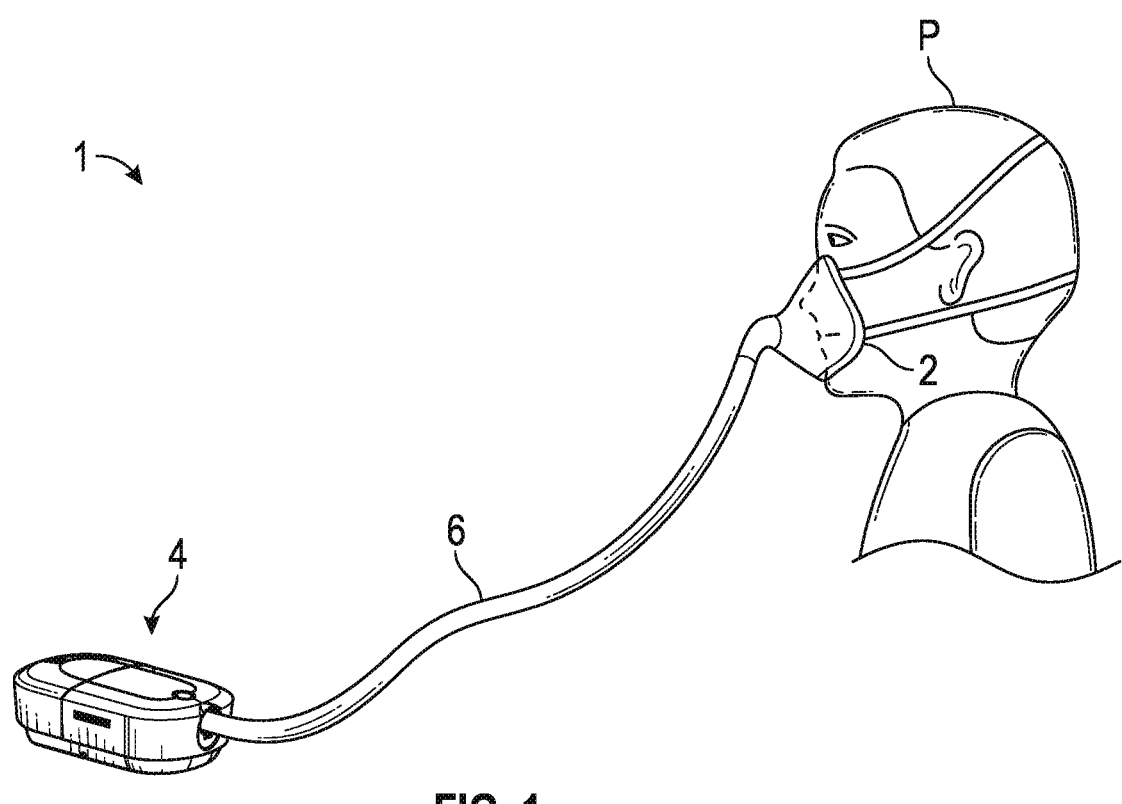
FIG. 1 is a simplified diagram of a respiratory therapy system according to an exemplary embodiment of the present invention shown with a patient interface device disposed on the face of a patient.

The present invention, as described in greater detail herein in connection with various particular exemplary embodiments, pertains to improvements in respiratory therapy machines for use with respiratory therapy systems for supplying a pressurized flow of breathable gas to an airway of a patient. In particular, the present invention pertains to positive airway pressure (PAP) respiratory therapy machines such as continuous positive airway pressure (CPAP) and BiLevel positive airway pressure (BiPAP) devices that include humidifiers. FIG. 1 is a simplified diagram of a respiratory therapy system 1 showing a patient interface 2 disposed on the face of a patient P. A respiratory therapy device 4, for example a CPAP machine, generates a pressurized flow of breathable gas to be delivered to the airway of patient P via a delivery conduit 6 operatively coupled to patient interface 2. While patient interface 2 is depicted as being a full face mask, it will be appreciated that the patient interface device may comprise a nasal/oral mask, nasal cushions, or any other type of interface without departing from the scope of the present invention.

Referring to FIGS. 2A-2C, in an exemplary embodiment of the present invention, respiratory therapy device 4 includes a pressure generator 10 and a humidifier 100. Pressure generator 10 takes in air from the ambient environment and outputs pressurized air via an output port 12 (shown in FIG. 2B) into humidifier 100. According to an exemplary embodiment, humidifier 100 includes a water tank 102 and a removable lid 104 selectively coupled thereto. When lid 104 is coupled to water tank 102, water tank 102 and lid 104 define a tank interior 106 therein that is structured to house both a volume of water 108 therein as well as a vapor region 110 therein (volume of water 108 and vapor region 110 are shown numbered in FIGS. 3B and 3C). Vapor region 110 is the region of tank interior 106, exclusive of a port arrangement 120 discussed below, that volume of water 108 does not occupy. As such, it will be appreciated that the volume of vapor region 110 is not fixed, as the volume of vapor region 110 is equal to the difference of the volume of tank interior 106 and the volume of water 108 contained in water tank 102. It will be further appreciated that the volume of vapor region 110 and the volume of water 108 contained in water tank 102 are inversely proportional.

Humidifier 100 is referred to hereinafter as being closed when lid 104 is disposed as shown in FIGS. 2A-2C, and it will be appreciated that lid 104 can be opened in order to add water to water tank 102. Lid 104 and water tank 102 can, for example and without limitation, each be constructed so as to enable lid 104 to be coupled to water tank 102 via a hinge 112 (shown in FIG. 2C) and to allow lid 104 to be selectively opened and closed via a latch 114 (shown in FIG. 2B) included on lid 104 that can snap fit onto a protrusion 116 included on water tank 102 in order to close water tank 102. It will be appreciated that any method suitable for coupling a lid to a container that enables the lid to be selectively opened can be used to couple lid 104 to water tank 102 without departing from the scope of the present invention.

Referring to FIGS. 2B and 2C, volume of water 108 in humidifier 100 can be heated via a heat source either included as a portion of or structured separately from humidifier 100. In the example embodiment described herein, a heat source 14 is provided in the form of a heating plate that is accompanied by electrical circuitry and power connections (not shown) such that heat source 14 can be selectively powered on and off by a user. In the embodiment of the respiratory therapy device 4 depicted in FIGS. 2A-2C, heat source 14 is a component coupled to the pressure generator 10, and the bottom (relative to the views shown in FIGS. 2A-2C) of humidifier 100 is produced to form a slot (the slot being unnumbered) into which heat source 14 can be inserted in order to couple pressure generator 10 and humidifier 100 together. It will be appreciated that the arrangement of respiratory therapy device 4 component bodies as shown in FIGS. 2B-2C represents just one possible manner in which heat source 14 can be included in the respiratory therapy device 4, and that heat source 14 can be included as part of humidifier 100 rather than pressure generator 10 or in any other suitable arrangement without departing from the scope of the present invention. It will be further appreciated that humidifier 100 and pressure generator 10 are said to be in an upright position when they are disposed as shown in FIGS. 2A-2C, i.e. with humidifier lid 104 coupled to the top of water tank 102 and with the bottom of water tank 102 positioned such that heat source 14 can be disposed underneath water tank 102.

In the example shown in FIGS. 2A-2C, a portion of the base of water tank 102 is formed by a metal plate 118 such that when the pressure generator 10 and humidifier 100 are coupled together as shown in FIG. 2A, heat source 14 is disposed below and in contact with metal plate 118. Powering on heat source 14 and heating metal plate 118 to a sufficiently high temperature heats volume of water 108, thus increasing the humidity and temperature of air in vapor region 110 (shown numbered in FIGS. 3B-3C).

Continuing to refer to FIGS. 2B and 2C as well as FIGS. 3A-3C, 5 and 6, passage of gas into and from the vapor region 110 of water tank 102 occurs through a port arrangement 120 (shown numbered in FIGS. 3A-3C) that extends inward from a wall of water tank 102 and is thus provided as a part of water tank 102. Port arrangement 120 includes an inlet passage 122, an outlet passage 124, and a number of drain passages 126 (described in detail with respect to FIG. 6 herein). Inlet passage 122 extends from a first end 128 (shown in FIGS. 2C and 3C) that is structured to receive the pressurized air output from output port 12 of pressure generator 10 to a second end 130 (shown in FIGS. 3A and 3C) opposite first end 128 at which the pressurized air exits inlet passage 122 and enters chimney 132. It will be appreciated that each of first end 128 and second end 130 form an opening in inlet passage 122, and as such, first end 128 may alternatively be referred to as first opening 128 and second end 130 may similarly alternatively be referred to as second opening 130 in subsequent descriptions of aspects of the present invention, depending on the context of the description. The air flow path that the pressurized air output from the pressure generator output port 12 takes after entering inlet passage 122 according to one example embodiment of the present invention is shown by arrows 201, 203 and 205 in FIGS. 3B and 3C.

The side of humidifier 100 that is disposed adjacent to the pressure generator 10 when humidifier 100 and pressure generator 10 are coupled as shown in FIG. 2A is referred to hereinafter as the "front" or "front side" of humidifier 100, and the side of humidifier 100 opposite the front side is referred to hereinafter as the "rear" or "rear side" of humidifier 100. FIG. 3B shows a sectional view of water tank 102 and port arrangement 120 as indicated by line 3B-3B in FIG. 3A. FIG. 3C shows a side sectional view of water tank 102 and port arrangement 120 as indicated by line 3C-3C in FIG. 3A. It will be appreciated that the front side of humidifier 100 is on the left side of FIG. 3C and that the rear side of humidifier 100 is on the right side of FIG. 3C.

Referring to FIGS. 3B and 3C, when pressure generator 10 outputs pressurized air into inlet passage 122, the pressurized air initially travels from first end 128 at the front side of humidifier 100 toward the rear side of humidifier 100, as depicted by arrows 201. Inlet passage 122 is produced with an elbow bend (not numbered) as shown in FIG. 3C, and once the pressurized air encounters the elbow bend, it proceeds to travel upward (relative to the orientation of the views shown in FIGS. 3B and 3C) toward the second end 130 of inlet passage 122. Port arrangement 120 further includes chimney 132 which is a tube-like structure that surrounds the portion of inlet passage 122 extending from the elbow of inlet passage 122 to second end 130 of inlet passage 122. Referring to FIG. 3C, it should be noted that the top (relative to the view shown in FIG. 3C) of chimney 132 extends above second end 130 of inlet passage 122 such that a top edge 134 of chimney 132 is disposed higher than second end 130 of inlet passage 122.

Referring to FIG. 4A, humidifier 100 includes a seal arrangement 170 which is coupled to a top edge 136 of water tank 102 and the top edges of port arrangement 120 (including top edge 134 of chimney 132) as indicated by the dashed lines in the figure. Seal arrangement 170 can, for example and without limitation, be formed by overmolding silicone onto a plastic substrate. In the example shown in the figures, seal arrangement 170 was formed in such manner and as such includes a plastic substrate 172 and a plurality of silicone portions 172 A-172C. While water tank 102 is shown with seal arrangement 170 removed in FIGS. 3A, 5, 6, 7, and 8 in order to better show details of port arrangement 120, it should be noted that seal arrangement 170 is coupled to water tank 102 (e.g., via an outer seal portion 172A) during manufacture such that seal arrangement 170 remains fixed in place, i.e. coupled to water tank 102 and top edges of port arrangement 120 (e.g., via inner seal portion 172B), when lid 104 is opened and closed. It will be further appreciated that when seal arrangement 170 is coupled to water tank 102 and port arrangement 120, a portion of inner seal arrangement 170 forms a cap 174 for chimney 132 such that the top (relative to the view shown in FIG. 4A) of chimney 132 is sealed off from the interior 106 of water tank 102. Seal arrangement 170 is designed to engage with the top (relative to the views shown in FIGS. 3B and 3C) surfaces of both water tank 102 and port arrangement 120 such that, when lid 104 is closed, seal arrangement 170 forms an air tight seal between the interior surface of lid 104 and top portions of water tank 102. In order to form a seal between lid 104 and seal arrangement 170 (and thus water tank 102), seal arrangement further includes an upward angled seal portion 172C that sealingly engages with the underside of lid 104 when lid 104 is coupled to water tank 102.

Referring again to FIGS. 3B and 3C and as previously stated, cap 174 seals off the top of chimney 132 from the tank interior 106, preventing the pressurized air exiting second end 130 of inlet passage 122 from flowing over top edge 134 of chimney 132 and directly into water tank 102 while also preventing water from entering chimney 132 over top edge 134. Instead, the pressurized air exiting second end 130 of inlet passage 122 is forced to flow downward as depicted by arrows 203 in FIG. 3B (rather than over top edge 134 of chimney 132) and out of a number of egress slots 138 (shown more clearly in FIGS. 5 and 8) of chimney 132, as further depicted by arrows 205 in FIG. 3B. Egress slots 138 are in fluid communication with tank interior 106, and it will be appreciated that the pressurized air flows into vapor region 110 of water tank 102 after flowing out of chimney 132 through egress slots 138.

Referring to FIGS. 3A and 5, port arrangement 120 comprises two lateral walls 140 disposed generally parallel to one another and disposed orthogonally to the front and rear sides of humidifier 100. A first of the two such lateral walls 140 can be viewed clearly in FIGS. 3A and 5. With respect to a plane containing line 3C-3C shown in FIG. 3A, said plane containing line 3C-3C being orthogonal to a plane containing the front side of humidifier 100, port arrangement 120 is reflectively symmetrical across said plane containing line 3C-3C, and as such, a second lateral wall 140 that is reflectively symmetrical to the first lateral wall 140 about said plane is disposed across from the first lateral wall 140. Outlet passage 124 includes a top edge 142, and a dip 144 in each lateral wall 140 between top edge 142 and top edge 134 of chimney 132 provides an opening in each lateral wall 140 such that vapor region 110 is in fluid communication with a first end 146 of outlet passage 124.

Referring to FIG. 3C and in accordance with an exemplary embodiment of the present invention, passage of the pressurized air through vapor region 110 results in humidification of the pressurized air. It will be appreciated that powering on heat source 14 heats volume of water 108 and the pressurized air in vapor region 110 and results in increased humidification of the pressurized air. The humidified pressurized air within vapor region 110 subsequently travels into outlet passage 124 (also depicted in FIG. 2C) through the openings created by dips 144 in the lateral walls 140. As depicted by arrows 207 in FIGS. 3B and 3C, the humidified pressurized air enters outlet passage 124 at first end 146 (also shown in FIG. 3A) and exits outlet passage 124 at a second end 148 (also shown in FIG. 2C) disposed opposite first end 146. Inner seal 170 ensures that the humidified pressurized air flows out of humidifier 100 via passage 124 by preventing the humidified pressurized air from flowing over top edge 136 of water tank 102 where lid 104 is coupled to water tank 102.

Referring to FIG. 2B, after exiting second end 148 of outlet passage 124, the humidified pressurized air re-enters pressure generator 10 through humidified input port 16. Referring to FIGS. 2B and 2C, the humidified pressurized air then subsequently exits pressure generator 10 via coupling 18, coupling 18 being structured to be coupled to delivery conduit 6 (shown in FIGS. 1 and 2A) such that the humidified pressurized air can be delivered to the airway of patient P via interface 2. FIGS. 1 and 2A depict coupling 18 as being coupled to conduit 6, and it will be appreciated that coupling 18 is not visible in the embodiment depicted in those figures because conduit 18 is inserted into a connector (not numbered) of conduit 6.

The elbow shape of inlet passage 122 and the snorkel-style arrangement of inlet passage 122 within chimney 132 that brings the pressurized air input to humidifier 100 in above the height of volume of water 108 contained within water tank 102, along with a gutter and drain channel system described in further detail with respect to FIGS. 6, 7, and 8 herein, presents an advantageous arrangement for preventing water in the water tank 102 from flowing into the pressure generator 10 without the use of volumetric ingress protection, i.e. without requiring that the volume of tank interior 106 far exceed volume of water 108 in order to have a location for the water to displace under conditions such as tilting, rotation, or other physical disturbance of the device. Accordingly, the present invention generally has at least either a smaller footprint or a smaller volume (if not both) than other respiratory therapy humidifiers and eliminates the supplemental protection such as a dry box or valve that is often required to render volumetric ingress protection devices effective.

In order to explain the how the snorkel-style arrangement of inlet passage 122 and gutter and drain channel system prevent the flow of water into the electromechanical components of pressure generator 10, the interior and exterior regions of both inlet passage 122 and chimney 132 must first be defined. Hereinafter, the region surrounded by the structure forming inlet passage 122 will be referred to as the "interior" of inlet passage 122 and the surface of the structure forming inlet passage 122 adjacent to the interior of inlet passage 122 will be referred to as the "interior surface" of inlet passage 122. Any region not interior to inlet passage 122 will hereinafter be referred to as "exterior" to inlet passage 122, and the surface of the structure forming inlet passage 122 adjacent to the exterior of inlet passage 122 will be referred to as the "exterior surface" of inlet passage 122. Similarly, the region surrounded by chimney 132 will be referred to as the "interior" of chimney 132 and the surface of the chimney 132 adjacent to the interior of chimney 132 will be referred to as the "interior surface" of chimney 132. Any region not interior to chimney 132 will hereinafter be referred to as "exterior" to chimney 132, and the surface of chimney 132 adjacent to the exterior of chimney 132 will be referred to as the "exterior surface" of chimney 132. In one non-limiting example, the region in which the pressurized air output by pressure generator 10 initially travels after being output to inlet passage 122 (as depicted by arrows 201 in FIGS. 3B and 3C) is the interior of inlet passage 122. In other non-limiting examples, inlet passage 122 is said to be disposed in the interior of chimney 132, and the region where arrows 203 are depicted in FIG. 3B is said to be exterior to inlet passage 122 and interior to chimney 132.

FIG. 6 shows a detail isometric view of a front portion of humidifier 100 with lid 104 removed wherein the water tank 102 and port arrangement 120 are viewed as if looking from the front side to the rear side of humidifier 100. As shown in FIG. 6, the cross-section of the portion of inlet passage 122 including first opening 128 is oblong such that first opening 128 is oblong, and first opening 128 is disposed in a plane perpendicular to the plane of the base of water tank 102, the base of water tank 102 including metal plate 118 (metal plate 118 being shown numbered in FIGS. 2C, 3B, and 5). Referring to FIG. 5 in addition to FIG. 6, it should be noted that the plane of first opening 128 is perpendicular to the plane in which second opening 130 of inlet 122 lies, the plane of second opening 130 being parallel to the plane of the base/metal plate 118 of water tank 102. In addition, the cross-section of the portion of inlet passage 122 including second opening 130 is rectangular such that second opening 130 is rectangular.

Referring still to FIG. 6, indicia 150 providing an indication of a maximum fill height of water for the water tank 102 is/are provided on water tank 102 to indicate to a user the recommended maximum height to fill water tank 102 with water when filling or refilling water tank 102. Referring to FIGS. 3A, 7, 9A, and 9B in addition to FIG. 6, each lateral wall 140 of port arrangement 120 includes a drain passage 126 disposed exterior to chimney 132 and adjacent to egress slot 138 that prevents water tank 102 from being overfilled to a level that could cause water to backflow into pressure generator 10 from inlet passage 122 in the event that a user fills the water tank 102 past the level indicated by indicia 150. Each drain passage 126 extends between an entry port 151 (shown in FIGS. 7 and 9B) disposed adjacent to corresponding egress slot 138 and an exit port 152 (shown in FIGS. 6, 7, 9A, and 9B) disposed opposite entry port 151, with exit port 152 being disposed in a plane containing the front side of water tank 102. It will be appreciated that each entry port 151 and exit port 152 form an opening to each drain passage 126 and that drain passages 126 are otherwise enclosed spaces.

FIG. 7 shows a sectional view of the humidifier of FIG. 4B along a non-central plane as indicated by line 7-7 in FIG. 4B in order to show how drain passages 126 divert excess water out of water tank 102 when the maximum fill height is exceeded. Lid 104 must be open for a user to be able to fill water tank 102 with water, and the interfaces between lid 104, water tank 102, and pressure generator 10 are designed such that lid 104 can only be opened when humidifier 100 is not coupled to pressure generator 10. That is, lid 104 can only be opened if humidifier 100 and pressure generator 10 are separated, such as shown in FIGS. 2B and 2C, and cannot be opened if humidifier 100 and pressure generator 10 are coupled, such as shown in FIG. 2A.

In FIG. 7, a dashed line 209 denotes the water level corresponding to maximum fill height indicia 150 shown in FIG. 6. When water tank 102 is disposed upright and a user fills water tank 102 with water, any water rising above dashed line 209 flows into each drain passage 126 at entry port 151 and flows through each drain passage 126 in the direction indicated by arrow 211, draining the excess water out of the front side of water tank 102 via exit port 152. Because humidifier 100 must be separated from pressure generator 10 in order to open lid 104 so that a user can fill water tank 102 with water, drain passages 126 provide an obvious indication of whether humidifier 100 can be coupled to pressure generator 10 for safe operation of respiratory therapy device 4. If there is no water draining out of the front side of water tank 102 via drain passages 126, humidifier 100 can be safely coupled to pressure generator 10, and if there is water draining out of drain passages 126, the user should wait until water stops draining out of drain passages 126 before coupling humidifier 100 to pressure generator 10.

While drain passages 126 prevent water from entering into inlet passage 122 due to an accidental overfill of water tank 102, referring to FIG. 8, a gutter 154 of chimney 132 prevents any water from volume of water 108 that enters chimney 132 via egress slots 138 during tilting, rotation, or other misuse of respiratory therapy device 4 (such water that enters into chimney 132 from volume of water 108 being referred to hereinafter as "encroaching water") from entering into inlet passage 122 and diverts such encroaching water back into volume of water 108. Referring briefly to FIG. 3B, gutter 154 is the bottom (relative to the view shown in FIG. 3B) portion of chimney 132, gutter 154 being the region disposed exterior to inlet passage 122, interior to chimney 132, and beneath the lowest edges of egress slots 138 in FIG. 3B. In FIG. 8, encroaching water 300 is represented by a number of line segments with arrowheads. Encroaching water 300 enters into chimney 132 via one egress slot 138, flows through gutter 154 and is channeled out of gutter 154 through the other egress slot 138 and back into volume of water 108.

The arrowheads used to depict encroaching water 300 in FIG. 8 are intended to be illustrative and not intended to suggest that encroaching water 300 flows in only one direction after entering into gutter 154. For example and without limitation, if respiratory therapy device 4 were being tilted rapidly back and forth, encroaching water 300 could exit out of the same egress slot 138 through which it entered into chimney 132, or some of the encroaching water 300 may exit out of one egress slot 138 while the rest of the encroaching water 300 exits out of the other egress slot 138, or water could alternately be entering through each of the egress slots 138. Gutter 154 is effective at preventing encroaching water 300 from entering into second end 130 of inlet passage 122 due to second end 130 being disposed sufficiently high above the bottom surface of gutter 154 that gutter 154 constitutes a path of least resistance for the flow of any encroaching water 300 during any rotation, tilting, or other physical disturbance of respiratory therapy device 4. In addition, it will be appreciated that water tank 102 is designed such that maximum fill height indicia 150 fall below the lowest edge of egress slots 138.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A water tank structured to hold a volume of water and humidify air output by a pressurized air generator, the water tank comprising:
   a port arrangement extending inward from a wall of the water tank to an interior of the water tank, the port arrangement comprising:
   an inlet comprising a passage having a first end of the inlet structured to receive pressurized air output by the pressurized air generator and a second end of the inlet disposed opposite the first end of the inlet, the second end of the inlet being disposed at a height above a maximum fill height of the water tank, wherein the first end of the inlet is disposed in a plane perpendicular to a plane of a base of the water tank;
   a chimney surrounding the second end of the inlet and comprising a number of egress slots disposed at a height lower than the second end of the inlet and in fluid communication with the interior of the water tank; and
   an outlet comprising a passage having a first end of the outlet in fluid communication with the interior of the water tank and a second end of the outlet disposed opposite the first end and in fluid communication with an exterior of the water tank,
   wherein a lowest edge of the number of egress slots is disposed at a height above the maximum fill height of the water tank, and
   wherein a portion of the water tank exclusive of the port arrangement and exclusive of the volume of water comprises a vapor region of the water tank,
   wherein the water tank further comprises a seal arrangement coupled to a top edge of the water tank and coupled to a top edge of the chimney such that the top edge of the chimney is sealed off from the interior of the water tank;
   wherein the seal arrangement is structured to engage a lid when the lid is coupled to the water tank in order to enclose the interior of the water tank; and
   wherein the seal arrangement is structured to prevent the pressurized air from flowing over the top edge of the chimney after flowing out of the second end of the inlet and to seal the interior of the water tank from the exterior of the water tank when the lid is coupled to the water tank and enclosing the water tank.

2. The water tank of claim 1, wherein the port arrangement further comprises a number of drain passages fluidly connecting the interior of the water tank to the exterior of the water tank and structured to drain water in excess of the maximum fill height from the interior of the water tank to the exterior of the water tank, and wherein the number of drain passages corresponds in number to the number of egress slots.

3. The water tank of claim 1, wherein a bottom surface of the chimney is disposed at a height lower than the height of the lowest edge of the number of egress slots, wherein the chimney comprises a gutter, the gutter being a region of the chimney disposed between a bottom surface of the chimney and the lowest edge of the number of egress slots and being disposed between an exterior of the inlet passage and an interior of the chimney, and wherein the second end of the inlet is disposed sufficiently higher than the gutter such that, in the event the water tank is physically disturbed, any water that enters the gutter is diverted by the gutter to flow back into the volume of water rather than into the second end of the inlet.

4. The water tank of claim 1, wherein a base of the water tank includes a metal plate structured to be disposed near a heat source.

5. The water tank of claim 1, wherein the port arrangement comprises a number of lateral walls corresponding in number to the number of egress slots, wherein each of the number of lateral walls connects to a top edge of the outlet and a top edge of the chimney, wherein a top edge of each of the number of lateral walls comprises a dip disposed between the top edge of the outlet and the top edge of the chimney, and wherein the dip in the top edge of each of the number of lateral walls provides an opening through which the first end of the outlet is in fluid communication with the interior of the water tank.

6. A humidifier structured to humidify air output by a pressurized air generator, the humidifier comprising:

a water tank structured to hold a volume of water, the water tank comprising:

a port arrangement extending inward from a wall of the water tank to an interior of the water tank, the port arrangement comprising:

an inlet comprising a passage having a first end of the inlet structured to receive pressurized air output by the pressurized air generator and a second end of the inlet disposed opposite the first end of the inlet, the second end of the inlet being disposed at a height above a maximum fill height of the water tank, wherein the first end of the inlet is disposed in a plane perpendicular to a plane of a base of the water tank;

a chimney surrounding the second end of the inlet and comprising a number of egress slots disposed at a height lower than the second end of the inlet and in fluid communication with the interior of the water tank; and an outlet comprising a passage having a first end of the outlet in fluid communication with the interior of the water tank and a second end of the outlet disposed opposite the first end of the outlet and in fluid communication with an exterior of the water tank; and a lid selectively coupled to the water tank in order to enclose the interior of the water tank, wherein a lowest edge of the number of egress slots is disposed at a height above the maximum fill height of the water tank, and wherein a portion of the water tank exclusive of the port arrangement and exclusive of the volume of water comprises a vapor region of the water tank;

wherein the water tank further comprises a seal arrangement coupled to a top edge of the water tank and coupled to a top edge of the chimney such that the top edge of the chimney is sealed off from the interior of the water tank;

wherein the seal arrangement is structured to engage the lid when the lid is coupled to the water tank in order to enclose the interior of the water tank; and wherein the seal arrangement is structured to prevent the pressurized air from flowing over the top edge of the chimney after flowing out of the second end of the inlet and to seal the interior of the water tank from the exterior of the water tank when the lid is coupled to the water tank and enclosing the water tank.

7. The humidifier of claim 6, wherein the water tank further comprises a number of drain passages fluidly connecting the interior of the water tank to the exterior of the water tank and structured to drain water in excess of the maximum fill height from the interior of the water tank to the exterior of the water tank, and wherein the number of drain passages corresponds in number to the number of egress slots.

8. The humidifier of claim 6, wherein a bottom surface of the chimney is disposed at a height lower than the height of the lowest edge of the number of egress slots, wherein the chimney comprises a gutter, the gutter being a region of the chimney disposed between a bottom surface of the chimney and the lowest edge of the number of egress slots and being disposed between an exterior of the inlet passage and an interior of the chimney, wherein the second end of the inlet is disposed sufficiently higher than the gutter such that, in the event the water tank is physically disturbed, any water that enters the gutter is diverted by the gutter to flow back into the volume of water rather than into the second end of the inlet.

9. The humidifier of claim 6, wherein a base of the water tank includes a metal plate structured to be disposed near a heat source.

10. The humidifier of claim 6 further comprising a heat source, wherein the heat source is structured to heat the volume of water, and wherein the heat source is structured to be selectively powered on.

11. The humidifier of claim 6, wherein the port arrangement comprises a number of lateral walls corresponding in number to the number of egress slots, wherein each of the number of lateral walls connects to a top edge of the outlet and a top edge of the chimney, wherein a top edge of each of the number of lateral walls comprises a dip disposed between the top edge of the outlet and the top edge of the chimney, and wherein the dip in the top edge of each of the number of lateral walls provides an opening through which the first end of the outlet is in fluid communication with the interior of the water tank.

12. A respiratory therapy device for providing humidified pressurized air to an airway of a patient, the respiratory therapy device comprising:

a pressurized air generator structured to output pressurized air;

a humidifier structured to humidify the pressurized air, the humidifier comprising:

a water tank structured to hold a volume of water, the water tank comprising:

a port arrangement extending inward from a wall of the water tank to an interior of the water tank, the port arrangement comprising:

an inlet comprising a passage having a first end of the inlet structured to receive the pressurized air output by the pressurized air generator and a second end of the inlet disposed opposite the first end of the inlet, the second end of the inlet being disposed at a height above a maximum fill height of the water tank;

a chimney surrounding the second end of the inlet and comprising a number of egress slots disposed at a height lower than the second end of the inlet and in fluid communication with the interior of the water tank; and an outlet comprising a passage having a first end of the outlet in fluid communication with the interior of the water tank and a second end of the outlet disposed opposite the first end of the outlet and in fluid communication with a conduit in fluid communication with the airway of the patient; and a lid selectively coupled to the water tank in order to enclose the interior of the water tank; and a heat source structured to heat the volume of water and to be selectively powered on, wherein a lowest edge of the number of egress slots is disposed at a height above the maximum fill height of the water tank, and wherein a portion of the water tank exclusive of the port arrangement and exclusive of the volume of water comprises a vapor region of the water tank, wherein the water tank further comprises a seal arrangement coupled to a top edge of the water tank and coupled to a top edge of the chimney such that the top edge of the chimney is sealed off from the interior of the water tank, wherein the seal arrangement is structured to engage the lid when the lid is coupled to the water tank in order to enclose the interior of the water tank, and wherein the seal arrangement is structured to prevent the pressurized air from flowing over the top edge of the chimney after flowing out of the second end of the inlet and to seal the interior of the water tank from the exterior of the water tank when the lid is coupled to the water tank and enclosing the water tank.

13. The respiratory therapy device of claim 12, wherein the water tank further comprises a number of drain passages fluidly connecting the interior of the water tank to the exterior of the water tank and structured to drain water in excess of the maximum fill height from the interior of the water tank to the exterior of the water tank, and wherein the number of drain passages corresponds in number to the number of egress slots.

14. The respiratory therapy device of claim 12, wherein a bottom surface of the chimney is disposed at a height lower than the height of the lowest edge of the number of egress slots, wherein the chimney comprises a gutter, the gutter being a region of the chimney disposed between a bottom surface of the chimney and the lowest edge of the number of egress slots and being disposed between an exterior of the inlet passage and an interior of the chimney, and wherein the second end of the inlet is disposed sufficiently higher than the gutter such that, in the event the water tank is physically disturbed, any water that enters the gutter is diverted by the gutter to flow back into the volume of water rather than into the second end of the inlet.

15. The respiratory therapy device of claim 12, wherein the heat source is fixedly coupled to the pressurized air generator, and wherein the humidifier is selectively coupled to the pressurized air generator.

16. The respiratory therapy device of claim 12, wherein the port arrangement comprises a number of lateral walls corresponding in number to the number of egress slots, wherein each of the number of lateral walls connects to a top edge of the outlet and a top edge of the chimney, wherein a top edge of each of the number of lateral walls comprises a dip disposed between the top edge of the outlet and the top edge of the chimney, and wherein the dip in the top edge of each of the number of lateral walls provides an opening through which the first end of the outlet is in fluid communication with the interior of the water tank.

* * * * *